(12) United States Patent
Hunneche et al.

(10) Patent No.: US 6,646,129 B2
(45) Date of Patent: Nov. 11, 2003

(54) CYANOGUANIDINES AS CELL PROLIFERATION INHIBITORS

(75) Inventors: Charlotte Schou Hunneche, Istanbul (TR); Erik Rytter Ottosen, Ølstykke (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 88 days.

(21) Appl. No.: 10/061,204

(22) Filed: Feb. 4, 2002

(65) Prior Publication Data

US 2002/0107400 A1 Aug. 8, 2002

Related U.S. Application Data

(62) Division of application No. 09/424,631, filed as application No. PCT/DK98/00193 on May 15, 1998, now Pat. No. 6,346,520.

(30) Foreign Application Priority Data

May 29, 1997 (GB) ............................................... 9711123

(51) Int. Cl.$^7$ ........................................... C07D 405/12
(52) U.S. Cl. ................................... 546/281.7; 546/306
(58) Field of Search ............................ 546/306, 282.1

(56) References Cited

U.S. PATENT DOCUMENTS 6,346,541 B1 * 2/2002 Hunneche .................... 546/286
6,525,077 B2 * 2/2003 Binderup et al. ............ 514/353

FOREIGN PATENT DOCUMENTS

WO  94-06770 A  3/1994

OTHER PUBLICATIONS

CA 137:379996, Binderup et al. 2002.*
SN 10/153,800, Madsen et al. 2002.*
CA 133:246880, Ekelund et al. 2000.*

* cited by examiner

*Primary Examiner*—Jane Fan
(74) *Attorney, Agent, or Firm*—Birch, Stewart, Kolasch & Birch, LLP

(57) ABSTRACT

The present invention relates to hitherto unknown compounds of formula (I) or their tautomeric forms,

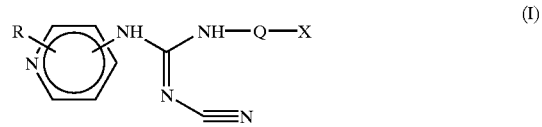

the attachment to the pyridine ring being in the 3- or 4-position, in which formula R stands for one or more substituents which can be the same or different and are selected from the group consisting of: hydrogen, halogen, trifluoromethyl, carboxy, $C_1$–$C_4$ alkyl, alkoxy or alkoxycarbonyl, nitro, amino or cyano and Q stands for $C_5$–$C_{14}$ divalent hydrocarbon radical which can be straight, branched, cyclic, saturated or unsaturated and X stands for carboxy, $C_1$–$C_4$ alkoxycarbonyl, di($C_1$–$C_4$ alkoxy)-phosphinoyloxy, amino, $C_1$–$C_4$ alkoxycarbonylamino or tetrahydropyranyloxy; and pharmaceutically acceptable, nontoxic salts and N-oxides thereof. The present compounds are of value in the human and veterinary practice.

6 Claims, No Drawings

CYANOGUANIDINES AS CELL PROLIFERATION INHIBITORS

This application is a divisional of application Ser. No. 09/424,631, filed on Nov. 26, 1999 now U.S. Pat. No. 6,346,520 and for which priority is claimed under 35 U.S.C. §120. application Ser. No. 09/424,631 is the national phase of PCT International Application No. PCT/DK98/00193 filed on May 15, 1998 under 35 U.S.C. §371. The entire contents of each of the above-identified applications are hereby incorporated by reference. This application also claims priority of Application No. 9711123.1 filed in United Kingdom on May 29, 1997 under 35 U.S.C. §119.

This invention relates to a hitherto unknown class of compounds which shows strong activity in inhibiting undesirable cell proliferation in e.g. skin cells and cancer cells, to pharmaceutical preparations containing these compounds, to dosage units of such preparations, and to their use in the treatment and prophylaxis of diseases characterized by abnormal cell differentiation and/or cell proliferation such as e.g. psoriasis and cancer.

The compounds of the present invention are represented by the general formula I

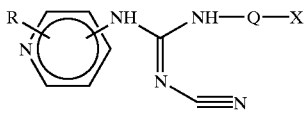

or their tautomeric forms, the attachment to the pyridine ring being in the 3- or 4-position, in which formula R stands for one or more substituents which can be the same or different and are selected from the group consisting of: hydrogen, halogen, trifluoromethyl, carboxy, $C_1$–$C_4$ alkyl, alkoxy or alkoxy-carbonyl, nitro, amino or cyano and Q stands for $C_5$–$C_{14}$ divalent hydro-carbon radical which can be straight, branched, cyclic, saturated or unsaturated and X stands for carboxy, amino, tetrahydropyranyloxy, $C_1$–$C_4$ saturated or unsaturated alkoxycarbonylamino, alkoxycarbonyl or di(alkoxy)phosphinoyloxy.

If the present compounds contain one or more asymmetric carbon atoms, these compounds may form optical isomers or diastereoisomers. The present invention also comprises such isomers, and mixtures of same.

The present salts of the compounds of formula I may be formed with pharmaceutically acceptable inorganic or organic acids, such as hydrochloric, hydrobromic and hydroiodic acid, phosphoric acid, sulfuric acid, nitric acid, 4-toluenesulfonic acid, methanesulfonic acid, formic acid, acetic acid, propionic acid, citric acid, tartaric acid, succinic acid, benzoic acid and maleic acid.

The present salts of the compounds of formula I may also be formed with pharmaceutically acceptable, inorganic or organic bases. Salts formed with pharmaceutically acceptable, non-toxic bases may be alkali metal salts and alkaline earth metal salts, such as lithium, sodium, potassium, magnesium, calcium salts, as well as salts with ammonia and suitable non-toxic amines, such as $C_1$–$C_6$-alkylamines, e.g. triethylamine, $C_1$–$C_6$ alkanolamines, e.g. diethanolamine or triethanolamine, procaine, cycloalkylamines, e.g. dicyclohexylamine, benzylamines, e.g. N-methyl-benzylamine, N-ethylbenzylamine, N-benzyl-2-phenylethylamine, N,N'-dibenzylethylenediamine or dibenzylamine, and heterocyclic amines, e.g. morpholine, N-ethylpiperidine and the like.

Even if the present compounds are well absorbed after enteral administration, in some cases it can be advantageous to prepare suitable bioreversible derivatives of compounds of the invention, i.e. to prepare so-called prodrugs, preferably derivatives, the physicochemical properties of which leads to improved solubility at physiological pH and/or absorption and/or bioavailability of the compound in question.

Such derivatives are for instance pyridyl N-oxide derivatives of compounds of the invention, such compounds being prepared by oxidation of the pyridyl N by a suitable oxidising agent, e.g. with 3-chloroperbenzoic acid in an inert solvent, e.g. dichloromethane.

Other suitable methods to improve the physicochemical properties and/or solubility of the compounds concerned can be used as well.

N-Alkyl-N'-cyano-N"-pyridylguanidines, described in United Kingdom Patent No. 1,489,879, are potent potassium channel activators with a pronounced effect as pre-capillary vasodilators, reducing the total peripheral resistance in animals and in man, and are thus useful as anti-hypertensives. As stated in International Patent No. PCT/DK93/00291, filing date Sep. 13, 1993, Publication No. WO 94/06770 the introduction of aryloxy-containing radicals into the aliphatic groups from the above-cited U.K. Patent has led to structures showing more specific pharmacological effects on isolated tissues and cells and with no or a negligible effect on $^{86}$Rb-efflux from potassium channels, as compared with the established effect of compounds covered by the above-mentioned U.K. Patent.

The compounds of the present invention inhibit the proliferation of various tumour cell lines in cultures at lower concentrations than the known compounds, confer Table 1 below, thus making them potentially useful in antineoplastic chemotherapy.

The inhibition of tumour cell proliferation was studied using different types of human cancer cell lines. The cell lines under investigation were small cell lung carcinoma (NYH), non small cell lung carcinoma (NCl-H460), and breast cancer (MCF-7) using the following general procedure:

The cells were cultured in vitro for 24 hours in the presence of the compound under investigation. DNA synthesis was measured by incorporation of [$^3$H]thymidine, and the median inhibitory concentrations ($IC_{50}$) of the compounds were calculated.

TABLE 1

Inhibition of tumour cell proliferation in vitro in human breast cancer (MCF-7), human small cell lung carcinoma (NYH) and human non small cell lung cancer (NCI-H460) cell lines by compounds of the following examples of the present invention.

| Compound from | MCF-7 $IC_{50}$ (nM) | NYH $IC_{50}$ (nM) | NCI-H460 $IC_{50}$ (nM) |
|---|---|---|---|
| Example No. 1 | 3.6 | 0.62 | 45 |
| Example No. 7 | 4.2 | 0.51 | 4.6 |
| Example No. 8 | 1.7 | 0.48 | 6.0 |
| Prior art A | 920 | 380 | >1000 |
| Prior art B | 250 | 45 | 67 |

A: N-Cyano-N'-(4-phenoxybutyl)-N"-4-pyridylguanidine, example 14 in PCT/DK93/00291.
B: N-Cyano-N'-(5-phenoxypentyl)-N"-4-pyridylguanidine, example 18 in PCT/DK93/00291.

The results show that the compounds of the present invention are able to inhibit the proliferation of tumour cells in vitro at lower concentrations than the compounds A and B from PCT/DK93/00291 .

The compounds of the invention are well tolerated and non-toxic and are exerting the described beneficial activities with no or minimal effect on the systemic blood pressure. In general, they may be administered by oral, intravenous, intraperitoneal, intranasal or transdermal routes.

The present invention also relates to methods for preparing the desired compounds of the general formula I. The compounds of the formula I may conveniently be prepared by standard procedures detailed in the art. The routes are outlined in the following reaction scheme.

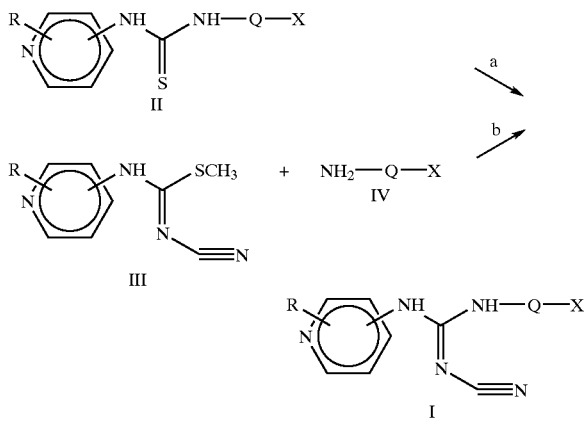

R, Q and X as defined above.

a) DCCD, $NH_2CN$, $Et_3N$, $CH_3CN$, 9 days. (General procedure 1).

b) DMAP, $Et_3N$, pyridine. (General procedure 2).

The present compounds are intended for use in pharmaceutical compositions which are useful in the treatment of the above mentioned diseases.

The amount required of a compound of formula (I) (hereinafter referred to as the active ingredient) for therapeutic effect will, of course, vary both with the particular compound, the route of administration and the mammal under treatment. A suitable dose of a compound of formula (I) for systemic treatment is 0.1 to 400 mg per kilogram bodyweight, the most preferred dosage being 1.0 to 100 mg per kg of mammal bodyweight, for example 5 to 20 mg/kg; administered once or more times daily.

A daily dose (for adults) may amount to 1 mg to 10000 mg, preferably from 70–5000 mg, and in the veterinary practice correspondingly, in daily doses from 0.1 to 400 mg/kg bodyweight.

While it is possible for an active ingredient to be administered alone as the raw chemical, it is preferable to present it as a pharmaceutical formulation. Conveniently, the active ingredient comprises from 0.1% to 99% by weight of the formulation. Conveniently, dosage units of a formulation contain between 0.5 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include those in a form suitable for oral, rectal, parenteral (including subcutaneous, intramuscular, intravenous and intraperitoneal) administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including antioxidants), emulsifying agents and the like.

The compositions may further contain other therapeutically active compounds usually applied in the treatment of the above mentioned pathological conditions, e.g. antineoplastic agents which may result in synergistic effects on tumour cells.

The invention will now be further described in the following general procedures and examples:

The exemplified compounds I are listed in table 2.

TABLE 2

| Compound No. | Example No. | R | 3- or 4-Pyridyl | Q | X |
|---|---|---|---|---|---|
| 101 | 1 | H | 4 | $(CH_2)_{12}$ | NH(CO)O-t-butyl |
| 102 | 2 | H | 4 | $(CH_2)_5$ | NH(CO)O-t-butyl |
| 103 | 3 | H | 4 | $(CH_2)_{12}$ | $NH_2$ |
| 104 | 4 | H | 4 | $(CH_2)_{10}$ | COOH |
| 105 | 5 | H | 4 | $(CH_2)_7$ | COOH |
| 106 | 6 | H | 4 | $(CH_2)_5$ | COOH |
| 107 | 7 | H | 4 | $(CH_2)_{11}$ | O-2-tetrahydropyranyl |
| 108 | 8 | H | 4 | $(CH_2)_{11}$ | $O(PO)(O-ethyl)_2$ |
| 109 | 9 | H | 4 | $(CH_2)_8$ | NH(CO)O-t-butyl |
| 110 | 10 | H | 4 | $(CH_2)_{10}$ | NH(CO)O-t-butyl |
| 111 | 11 | 2-$CH_3$ | 4 | $(CH_2)_{10}$ | NH(CO)O-t-butyl |
| 112 | 12 | 6-$OCH_3$ | 3 | $(CH_2)_{10}$ | NH(CO)O-t-butyl |
| 113 | 13 | 6-$OCH_3$ | 3 | $(CH_2)_{10}$ | $NH_2$ |
| 114 | 14 | H | 4 | $(CH_2)_{10}$ | NH(CO)O-n-butyl |
| 115 | 15 | H | 4 | $(CH_2)_6$ | O-2-tetrahydropyranyl |
| 116 | 16 | H | 4 | $(CH_2)_6$ | $O(PO)(O-ethyl)_2$ |

TABLE 2-continued

| Compound No. | Example No. | R | 3- or 4- Pyridyl | Q | X |
|---|---|---|---|---|---|
| 117 | 17 | H | 4 | (CH$_2$)$_8$ | O-2-tetrahydropyranyl |
| 118 | 18 | H | 4 | (CH$_2$)$_9$ | O(PO)(O-ethyl)$_2$ |
| 119 | 19 | 6-OCH$_3$ | 3 | (CH$_2$)$_{11}$ | O-2-tetrahydropyranyl |
| 120 | 20 | H | 4 | (CH$_2$)$_{10}$ | NH(CO)O-allyl |

All melting points are uncorrected. For $^1$H and $^{13}$C nuclear magnetic resonance (NMR) spectra (300 MHz) chemical shift values (δ) are quoted, unless otherwise specified, for deuterochloroform and hexadeuterodimethylsulfoxide solutions relative to internal chloroform ($^1$H NMR δ7.25. $^{13}$C NMR δ76.81) or tetramethylsilane (δ0.00). The value for a multiplet (m), either defined (doublet (d), triplet (t), quartet (q)) or not at the approximate mid point is given unless a range is quoted (s singlet, b brod). Chromatography was performed on silica gel. The following abbreviations and formulas are used: DCCD (N,N'-dicyclohexylcarbodiimine), NH$_2$CN (cyanamide), Et$_3$N (triethylamine), CH$_3$CN (acetonitrile), DMAP (dimethylaminopyridine), MeOH (methanol), CH$_2$Cl$_2$ (methylene-chloride,) EtOAc (ethylacetate), NH$_3$ (ammonia), CDCl$_3$ (deuterochloroform) and DMSO-d$_6$ (hexadeuterodimethylsulfoxide).

General Procedure 1

Conversion of Compounds of the General Formula II Into Compounds of the General Formula I A compound of the general formula II (5 mmol) was suspended in acetonitrile (12 ml) and dicyclohexylcarbodiimide (10 mmol), cyanamide (10 mmol) and triethylamine (0.07 ml) was added. The reaction mixture was stirred at room temperature for 9 days.

The reaction mixture was filtered and washed with acetonitrile. The crude product was purified by flash chromatography (Eluent: 0–7% MeOH in CH$_2$Cl$_2$) and crystallized from ether to give the product of general formula I as white crystals.

General Procedure 2

Coupling of Compounds of the General Formula III with Compounds of the General Formula IV Resulting in Compounds of the General Formula I A compound of the general formula III (4 mmol), a compound of the general formula IV (5 mmol), triethylamine (0.12 ml) and 4-dimethylamino-pyridine (15 mg) were dissolved in pyridine (4 ml). The reaction mixture was stirred at 60° C. for 11 hours and then cooled to room temperature.

The product was precipitated with ether. Filtration resulted in pure product of the general formula I as white crystals.

EXAMPLE 1

N-(1 2-t-Butoxycarbonylaminododecyl)-N'-cyano-N"-4-pyridylguanidine (Compound 101)

General procedure 1.
Starting compound II: N-(12-t-Butoxycarbonylaminododecyl)N-4-pyridylthiourea.
Purification: General procedure.
$^{13}$C NMR (DMSO-d$_6$)δ: 157.1, 155.5,150.0, 145.9, 116.4, 114.5, 77.2, 48.6, 41.8, 29.4, 29.0, 28.6, 28.2, 26.2, 26.1.

EXAMPLE 2

N-(5-t-Butoxycarbonylaminopentyl)-N'-cyano-N"-4-pyridylguanidine (Compound 102)

General procedure 1.
Starting compound II: N-(5-t-butoxycarbonylaminopentyl)-N-4-pyridylthiourea.
Purification: General procedure.
$^1$H NMR (DMSO-d$_6$)δ: 9.37 (bs, 1H), 8.38 (d, 2H), 7.81 (bs, 1H), 7.21 (bd, 2H), 6.77 (t, 1H), 3.25 (m, 2H), 2.91 (q, 2H), 1.52 (m, 2H), 1.45–1.20 (m, 4H), 1.37 (s, 9H).

EXAMPLE 3

N-(12-Aminododecyl-N'-cyano-N"-pyridylguanidine (Compound 103)

General procedure 2. Reaction time 2 days at room temperature.
Starting compound III: S-Methyl N-cyano-N'-4-pyridylisothiourea.
Starting compound IV: 1,12-Diaminododecyl.
Purification: Flash chromatography (Eluent 0–30% MeOH in CH$_2$Cl$_2$).
$^1$H NMR (DMSO-d$_6$)δ: 8.30 (bs, 2H), 7.18 (bs, 2H), 3.30 (m, 2H), 2.88 (m, 2H), 1.60–1.00 (m, 22H).

EXAMPLE 4

N-(10-Carboxydecyl)-N'-cyano-N"-4-pyridylguanidine (Compound 104)

General procedure 2.
Starting compound III: S-Methyl N-cyano-N'-4-pyridylisothiourea.
Starting compound IV: 11-Aminoundecanoic acid.
Purification: The remaining 11-aminoundecanoic acid was precipitated with ether. After filtration the filtrate was concentrated and the residue was stirred with water. After a second filtration the filtrate contained almost pure product. Evaporation in vacuo and crystallization from acetonitrile resulted in the pure product.
$^1$H NMR (DMSO-d$_6$)δ: 8.38 (d, 2H), 8.03 (bs, 1H), 7.21 (bd, 2H), 3.26 (q, 2H), 2.17 (t, 2H), 1.50 (m, 4H), 1.25 (bs, 12H).

EXAMPLE 5

N-(7-Carboxyheptyl)-N'-cyano-N"-4-pyridylguanidine (Compound 105)

General procedure 2.
Starting compound III: S-Methyl N-cyano-N'-4-pyridylisothiourea.
Starting compound IV: 8-Aminooctanoic acid.
Purification: Flash chromatography (Eluent 0–100% MeOH in CH$_2$Cl$_2$) and crystallization from acetonitrile.
$^{13}$C NMR (DMSO-d$_6$)δ: 174.7, 157.2, 149.8, 146.1, 116.3, 114.4, 41.7, 33.8, 28.6, 28.4, 28.3, 26.0, 24.5.

EXAMPLE 6

N-(5-Carboxypentyl)-N'-cyano-N"-4-pyridylguanidine (Compound 106)

General procedure 2. Reaction time 14 days at room temperature.
Starting compound III: S-Methyl N-cyano-N'-4-pyridylisothiourea.
Starting compound IV: 6-Aminohexanoic acid.
Purification: Flash chromatography (Eluent 0–55% MeOH in CH$_2$Cl$_2$) and crystallization from acetone/water.
$^{13}$C NMR (DMSO-d$_6$)δ: 175.0, 157.2, 149.8, 146.1, 116.4, 114.5, 41.6, 34.0, 28.4, 25.7, 24.2.

EXAMPLE 7

N-Cyano-N'-4-pyridyl-N"-(11-tetrahydropyranyloxyundecanyl)guanidine (Compound 107)

General procedure 2. Reaction time 14 days at room temperature.

Starting compound III; S-Methyl N-cyano-N'-pyridylisothiourea.

Starting compound IV: 11-Tetrahydropyranyloxyundacanylamine.

Purification: Flash chromatography (Eluent $CH_2Cl_2$/MeOH/$NH_3$(aq) 95:5:0.5) followed by trituration in ether.

$^{13}$C NMR (DMSO-$d_6$)δ: 157.5, 150.9, 144.8, 117.0, 115.9, 99.1, 67.8, 62.6, 42.6, 30.9, 29.7, 29.5, 29.4, 29.2, 26.8, 26.2, 25.5, 19.8.

EXAMPLE 8

N-Cyano-N'-(11-diethylphosphinoyloxyundecanyl)-N"-4-pyridylguanidine (Compound 108)

General procedure 2. Reaction time 14 days at room temperature.

Starting compound III: S-Methyl N-cyano-N'-4-pyridylisothiourea.

Starting compound IV: Diethyl 11-aminoundecanylphosphate.

Purification: Flash chromatography (Eluent EtOAc/MeOH/$NH_3$(aq) 100:5:0.2 followed by 50:5:0.1). The compound was obtained as a yellow oil.

$^{13}$C NMR (CDCl$_3$)δ: 157.4, 150.5, 145.3, 116.9, 115.3, 67.9, 67.9, 63.9, 63.9, 42.7, 30.2, 30.1, 29.3, 29.2, 29.1, 29.0, 28.8, 26.6, 25.2, 16.2,

EXAMPLE 9

N-(8-t-Butoxycarbonylaminooctyl-N'-cyano-N"-4-pyridylguanidine (Compound 109)

General procedure 2.

Starting compound III: S-Methyl N-cyano-N'-4-pyridylisothiourea.

Starting compound IV: 8-t-Butoxycarbonylaminooctylamine.

Purification: General procedure.

$^{13}$C NMR (CDCl$_3$)δ: 157.3, 155.5, 149.8, 146.1, 116.4, 114.5, 77.2, 41.7, 29.4, 28.6, 28.6, 28.2, 26.1, 26.0.

EXAMPLE 10

N-(10-t-Butoxycarbonylaminodecyl-N'-cyano-N"-4-pyridylguanidine (Compound 110)

General procedure 2.

Starting compound III: S-Methyl N-cyano-N'-4-pyridylisothiourea.

Starting compound IV: 10-t-Butoxycarbonylaminodecylamine.

Purification: General procedure.

$^{13}$C NMR (CDCl$_3$)δ: 157.3, 155.5, 149.8, 146.0, 116.4, 114.5, 77.2, 41.7, 29.4, 28.8, 28.8, 28.6, 28.5, 28.2, 26.2, 26.1.

EXAMPLE 11

N-(10-t-Butoxycarbonylaminodecyl)-N'-cyano-N"-(2-methyl-4-pyridyl)-guanidine (Compound 111)

General procedure 2.

Starting compound III: S-Methyl N-cyano-N'-(2-methyl4-pyridyl)-isothiourea.

Starting compound IV: 10-t-Butoxycarbonylaminodecylamine.

Purification: Flash chromatography (Eluent 1% $NH_3$(aq) and 0–10% MeOH in $CH_2Cl_2$). The compound was obtained as a yellow oil.

$^{13}$C NMR (CDCl$_3$)δ: 1.58.1, 157.3, 155.5, 149.4, 146.2, 116.5, 113.5, 112.0, 77.2, 41.7, 29.4, 28.9, 28.8, 28.6, 28.6, 28.6, 28.2, 26.2, 26.1, 24.0.

EXAMPLE 12

N-(10-t-Butoxycarbonylaminodecyl)-N'-cyano-N"-(2-methoxy-5pyridyl)guanidine (Compound 112)

General procedure 2.

Starting compound III: S-Methyl N-cyano-N'-(2-methoxy-5-pyridyl)-isothiourea.

Starting compound IV: 10t-Butoxycarbonylaminodecylamine.

Purification: Flash chromatography (Eluent 1% $NH_3$(aq) and 0–6% MeOH in $CH_2Cl_2$) and crystallization from ether.

$^{13}$C NMR (CDCl$_3$)δ: 161.2, 158.6, 155.5, 143.3, 137.0, 127.9, 117.3, 110.3, 77.2, 53.2, 41.3, 29.4, 28.9, 28.8, 28.8, 28.6, 28.6, 28.2, 26.2, 26.1.

EXAMPLE 13

N-(10-Aminodecyl)-N'-cyano-N"-(2-methoxy-5pyridyl)guanidine (Compound 113)

General procedure 2.

Starting compound III: S-Methyl N-cyano-N'-(2-methoxy-5-pyridyl)-isothiourea.

Starting compound IV: 1,10-Diaminodecane.

Purification: Flash chromatography (Eluent EtOAc/MeOH, 6:1 and then EtOAc/MeOH/$NH_3$(aq) 6:1:1).

$^{13}$C NMR (CDCl$_3$)δ: 161.1, 158.5, 143.2, 136.9, 128.0, 117.3, 110.3, 53.2, 41.3, 41.0, 32.0, 28.9, 28.8, 28.8, 28.6, 26.2, 26.0.

EXAMPLE 14

N-(10-n-Butoxycarbonylaminodecyl)-N'-cyano-N"-4-pyridylguanidine (Compound 114)

General procedure 2.

Starting compound III: S-Methyl N-cyano-N'-4-pyridylisothiourea.

Starting compound IV: 10-n-Butoxycarbonylaminodecylamine.

Purification: Flash chromatography (Eluent 5–100% EtOAc in petroleum ether) and crystallization from ether.

$^{13}$C NMR (CDCl$_3$)δ: 157.0, 156.3, 150.1, 145.8, 116.3, 114.5, 63.1, 41.7, 30.7, 29.3, 28.8, 28.8, 28.6, 28.5, 26.1, 26.1, 18.5, 13.5.

EXAMPLE 15

N-Cyano-N'-4-pyridyl-N"-(6-tetrahydropyranyloxyhexyl)guanidine (Compound 115)

General procedure 2. Reaction time 4 days at 60° C.

Starting compound III: S-Methyl N-cyano-N'-4-pyridylisothiourea.

Starting compound IV: 6-Tetrahydropyranyloxyhexylamine.

Purification: Flash chromatography (Eluent $CH_2Cl_2$/MeOH/$NH_3$(aq) 98:2:0.2 and then 95:5:0.5), trituration in petroleum ether and then recrystallization from EtOAc.

$^{13}$C NMR (CDCl$_3$)δ: 157.3, 149.8, 146.0, 116.4, 114.5, 97.9, 66.4, 61.2, 41.7, 30.3, 29.1, 28.6, 25.9, 25.3, 25.0, 19.2.

EXAMPLE 16

N-Cyano-N'-(6-diethylphosphinoyloxyhexyl)-N''-4-pyridylguanidine (Compound 116)

General procedure 2. Reaction time 4 days at 60° C.
Starting compound III: S-Methyl N-cyano-N'-4-pyridylisothiourea.
Starting compound IV: 6-Diethylphosphinoyloxyhexylamine.
Purification: Flash chromatography (Eluent $CH_2Cl_2$/MeOH/$NH_3$(aq) 98:2:0.2 and then 95:5:0.5).
13C NMR (CDCl3)δ: 157.1, 150.0, 116.4, 114.5, 66.7, 63.0, 41.6, 29.5, 28.4, 25.6, 24.5, 15.9.

EXAMPLE 17

N-Cyano-N'-4-pyridyl-N''-(8-tetrahydropyranyloxyoctyl)guanidine (Compound 117)

General procedure 2. Reaction time 4 days at 60° C.
Starting compound III: S-Methyl N-cyano-N'-4-pyridylisothiourea.
Starting compound IV: 8-Tetrahydropyranyloxyoctylamine.
Purification: Flash chromatography (Eluent $CH_2Cl_2$/MeOH/$NH_3$(aq) 98:2:0.2) and crystallization from EtOAc.
$^{13}$C NMR (CDCl3)δ: 157.3, 150.0, 146.1, 116.5, 114.6, 98.0, 66.6, 61.3, 41.8, 30.4, 29.2, 28.8, 28.7, 28.7, 26.2, 25.7, 25.1, 19.3.

EXAMPLE 18

N-Cyano-N'-(9-diethylphosphinoyloxynonyl-N''-4-pyridylguanidine (Compound 118)

General procedure 2. Reaction time 4 days at 60° C.
Starting compound III: S-Methyl N-cyano-N'-4-pyridylisothiourea.
Starting compound IV: 9-Diethylphosphinoyloxynonylamine.
Purification: Flash chromatography (Eluent EtOAc/EtOH/$NH_3$(aq) 30:3:0.2 and then 25:5:0.2).
$^{13}$C NMR (CDCl$_3$)δ: 157.2, 149.9, 146.0, 116.4, 114.5, 66.8, 63.0, 41.7, 29.6, 28.7, 28.6, 28.5, 28.3, 26.0, 24.8, 15.9.

EXAMPLE 19

N-Cyano-N'-(2-methoxy-5-pyridyl-N''-(11-tetrahydropyranyloxy-undecanyl)guanidine (Compound 119)

General procedure 2. Reaction time 4 days at 60° C.
Starting compound III: S-Methyl N-cyano-N'-(2methoxy-5pyridyl)-isothiourea.
Starting compound IV: 11-Tetrahydropyranyloxyundecanylamine.
Purification: Flash chromatography (Eluent $CH_2Cl_2$/MeOH/$NH_3$(aq) 98:2:0.2).
$^{13}$C NMR (CDCl$_3$)δ: 163.5, 159.4, 145.4, 137.6, 125.3, 117.8, 112.2, 98.9, 67.7, 62.4, 54.0, 42.1, 30.8, 29.8, 29.5, 29.5, 29.4, 29.3, 29.2, 26.7, 26.2, 25.5, 19.8.

EXAMPLE 20

N-(10-Allyloxycarbonylaminodecyl)-N'-cyano-N''-4-pyridylguanidine (Compound 120)

General procedure 2.
Starting compound III: S-Methyl N-cyano-N'-4-pyridylisothiourea.
Starting compound IV: 10-Allyloxycarbonylaminodecylamine.
Purification: Flash chromatography (Eluent 0.5% $NH_3$ (aq) and 0–13% MeOH in $CH_2Cl_2$) and crystallization from acetone/ether.

$^{13}$C NMR (CDCl$_3$)δ: 157.08, 155.81, 150.06, 145.77, 133.83, 116.66, 116.37, 114.46, 63.97, 41.72, 40.13, 29.31, 28.85, 28.82, 28.62, 28.61, 28.56, 26.13, 26.08

EXAMPLE 21

Capsules
1 Capsule contains:

| | |
|---|---|
| N-(12-t-Butoxycarbonylaminododecyl)-N'-cyano-N''-4-pyridylguanidine (active compound) | 100 mg |
| Polyethylene Glycol | 962 mg |
| Gelatine Capsule no. 00 | 122 mg |
| Gelatine | |

EXAMPLE 22

Tablets
Manufacture of 10,000 tablets

| | | |
|---|---|---|
| I | N-(12-t-Butoxycarbonylaminododecyl)-N'-cyano-N''-4-pyridylguanidine (active compound) | 10,000 kg |
| | Cross carmellose sodium | 0,300 kg |
| II | Hydroxypropylmethyl cellulose, low viscosity type | 0,200 kg |
| | Sorbimacrogol oleate | 0,010 kg |
| | Purified water | q.s. |
| III | Crosscarmellose sodium | 0,200 kg |
| | Coloidal anhydrous silica | 0,050 kg |
| | Magnesium stearate | 0,050 kg |

I is mixed intimately in a highshear mixer, is wetted with II and granulated into a moist mass. The moist granulate is dried in a fluid-bed dryer at an inlet air temperature of 60° C. until the dried granulate has a water activity of 0.3–0.4 (=in equilibrium with air of 3040% R.H.).

The dried granulate is passed through a sieve with mesh openings of 850 mm.

The sieved granulate is finally mixed with III in a cone mixer.

The finished granulate is compressed into tablets of mass 1071 mg and sufficient hardness.

What we claim is:

1. A compound of the formula I,

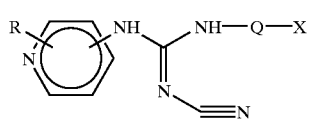

or their tautomeric forms, the attachment to the pyridine ring being in the 3- or 4-position, in which formula R stands for one or more substituents which can be the same or different and are selected from the group consisting of: hydrogen, halogen, trifluoromethyl, carboxy, $C_1$–$C_4$ alkyl, alkoxy or alkoxy-carbonyl, nitro, amino or cyano and Q stands for $C_5$–$C_{14}$ divalent hydrocarbon radical which can be straight, branched, cyclic, saturated or unsaturated and X stands for carboxy, amino, tetrahydropyranyloxy, $C_1$–$C_4$ saturated or unsaturated alkoxycarbonylamino, or alkoxycarbonyl; or a pharmaceutically acceptable, non-toxic salt or an N-oxide thereof.

2. A compound according to formula I of claim 1, in which the attachment to the pyridine ring is in the 4-position, in which formula R stands for hydrogen and Q stands for $C_5$–$C_{12}$ divalent hydrocarbon radical which can be straight, branched, saturated or unsaturated and X stands for carboxy, amino, tetrahydropyranyloxy, $C_1$–$C_4$ saturated or unsaturated alkoxycarbonylamino, or alkoxycarbonyl; or a pharmaceutically acceptable, non-toxic salt or an N-oxide thereof.

3. A salt according to claim 1 in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, and lithium, sodium, potassium, magnesium, calcium salts, as well as salts with ammonia, $C_1$–$C_6$-alkylamines, $C_1$–$C_6$ alkanolamines, procaine, cycloalkylamines, benzylamines, and heterocyclic amines.

4. A compound of claim 1 which is selected from the group consisting of:

N-(12-t-butoxycarbonylaminododecyl)-N'-cyano-N"-4-pyridylguanidine;

N-cyano-N'-4-pyridyl-N"-(11-tetrahydropyranyloxyundecanyl) guanidine;

N-(8-t-butoxycarbonylaminooctyl)-N'-cyano-N"-4-pyridylguanidine;

N-cyano-N'-4-pyridyl-N"-(8-tetrahydropyranyloxyoctyl) guanidine;

or a salt or pure enantiomeric form thereof.

5. A pharmaceutical composition comprising a compound according to claim 1 together with a pharmaceutically acceptable carrier thereof.

6. Method for producing a compound of formula I according to claim 1, in which a) a compound of the general formula II

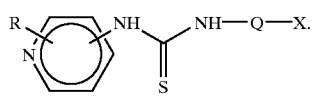

in which R, Q and X are as defined above, is reacted with dicyclohexyl-carbodiimide and cyanamide in the presence of triethylamine or another tertiary amine in acetonitrile or another inert solvent at room temperature or above; or b) a compound of the general formula III

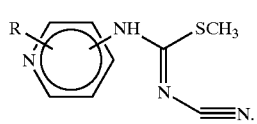

in which R is as defined above, is reacted with a compound of the general formula IV

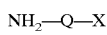

in which Q and X are as defined above, in the presence of triethylamine or another tertiary amine and 4-dimethylaminopyridine in pyridine or an inert solvent at room temperature or above.

* * * * *